(12) United States Patent
Nishijima et al.

(10) Patent No.: US 9,958,412 B2
(45) Date of Patent: May 1, 2018

(54) GAS SENSOR ELEMENT

(71) Applicants: TOYOTA JIDOSHA KABUSHIKI KAISHA, Toyota-shi, Aichi (JP); DENSO CORPORATION, Kariya-shi, Aichi (JP)

(72) Inventors: Hiroki Nishijima, Nisshin (JP); Yoshiharu Miyake, Miyoshi (JP); Haruki Kondo, Okazaki (JP); Makoto Nakae, Nagoya (JP); Tooru Takeuchi, Kariya (JP); Masayuki Tamura, Handa (JP); Atsushi Murai, Kuwana (JP)

(73) Assignees: TOYOTA JIDOSHA KABUSHIKI KAISHA, Toyota-shi, Aichi (JP); DENSO CORPORATION, Kariya-shi, Aichi (JP)

( * ) Notice: Subject to any disclaimer, the term of this patent is extended or adjusted under 35 U.S.C. 154(b) by 162 days.

(21) Appl. No.: 14/793,211

(22) Filed: Jul. 7, 2015

(65) Prior Publication Data
US 2016/0018357 A1    Jan. 21, 2016

(30) Foreign Application Priority Data

Jul. 18, 2014 (JP) ................................ 2014-147482
Apr. 28, 2015 (JP) ................................ 2015-091445

(51) Int. Cl.
*G01N 27/407* (2006.01)
*G01N 27/406* (2006.01)
*G01N 27/409* (2006.01)

(52) U.S. Cl.
CPC ..... *G01N 27/4067* (2013.01); *G01N 27/4071* (2013.01); *G01N 27/409* (2013.01); *G01N 27/4077* (2013.01)

(58) Field of Classification Search
CPC ............ G01N 27/4067; G01N 27/409; G01N 27/4077
See application file for complete search history.

(56) References Cited

U.S. PATENT DOCUMENTS

| 2003/0159928 | A1 | 8/2003 | Kojima et al. |
| 2010/0155240 | A1 | 6/2010 | Matsuoka et al. |
| 2014/0291150 | A1 | 10/2014 | Otsuka et al. |

FOREIGN PATENT DOCUMENTS

| DE | 103 08 558 A1 | 4/2004 |
| JP | 2009-80110 A | 4/2009 |

(Continued)

OTHER PUBLICATIONS

Eglish translation of JP 2012-093330 A from EPO website.*

(Continued)

*Primary Examiner* — J. Christopher Ball
(74) *Attorney, Agent, or Firm* — Sughrue Mion, PLLC

(57) ABSTRACT

A gas sensor element having a porous protective layer with excellent water repellency. Provided is a gas sensor element having a detection portion, which has a stack of a solid electrolyte body having a pair of electrodes on opposite sides thereof and a heat generating body including a heat generating source, and a porous protective layer formed around the detection portion. The porous protective layer has thermal conductivity λ in the range of 0.2 to 5 W/mK, and has λCpρ, which is the product of the thermal conductivity λ(W/mK), density ρ(g/m³), and specific heat Cp(J/gK), in the range of $5.3 \times 10^5$ to $2.1 \times 10^7$ WJ/m⁴K².

5 Claims, 6 Drawing Sheets

(56) References Cited

FOREIGN PATENT DOCUMENTS

| JP | 200980111 A | 4/2009 |
|----|-------------|--------|
| JP | 2010-169655 A | 8/2010 |
| JP | 2011-237222 A | 11/2011 |
| JP | 2011-252894 A | 12/2011 |
| JP | 2012-93330 A | 5/2012 |
| WO | 2011/138652 A1 | 11/2011 |

OTHER PUBLICATIONS

"Characteristics of Kyocera Technical Ceramics", Datasheet [online], Kyocera Corporation, Jul. 2012, URL: http://web.archive.org/web/20121115045330/http://global.kyocera.com/prdct/fc/product/pdf/material.pdf. (8 pages total).

* cited by examiner

GAS SENSOR ELEMENT

CLAIM OF PRIORITY

The present application claims priority from Japanese patent applications JP 2014-147482 filed on Jul. 18, 2014, JP 2015-091445 filed on Apr. 28, 2015, the contents of which are hereby incorporated by reference into this application.

BACKGROUND

Technical Field

The present invention relates to a gas sensor element that is mounted on a vehicle, for example, and detects the concentration of oxygen in exhaust gas.

Background Art

In a variety of industries, a variety of attempts has been made worldwide to reduce environmental impacts and burdens. In particular, in the automobile industry, development for promoting the spread of not only fuel-efficient gasoline engine vehicles, but also so-called eco-friendly vehicles, such as hybrid vehicles or electric vehicles, as well as for further improving the performance of such vehicles has been advanced day by day.

Purification of exhaust gas and improvement of fuel economy performance of vehicles have been conducted by detecting the concentration of oxygen in a measurement target gas, such as exhaust gas, using a gas sensor and precisely controlling the fuel oil consumption and the intake air amount.

An exemplary basic configuration of a gas sensor element that constitutes such a gas sensor includes a detection portion, which has a stack of a solid electrolyte body having a pair of electrodes on opposite sides thereof and a heat generating body including a heat generating source, and a porous protective layer formed around the detection portion.

A gas sensor detects the concentration of oxygen in exhaust gas at a temperature as high as about 400 to 850° C. Thus, if water droplets (i.e., condensed water) in the exhaust gas collide with the gas sensor element that constitute the gas sensor, it is concerned that thermal shock may be generated due to partial quenching, and due to a change in the volume of the element with a change in the temperature, an abnormal output resulting from a temperature drop when the element becomes wet may be generated or an abnormal output resulting from cracking of the element due to the thermal shock may be generated. Further, it is also concerned that metallic compounds in the condensed water may infiltrate the element together with the water, which in turn can poison the detection portion of the gas sensor element.

In order to eliminate such concerns, a porous protective layer is provided around the detection portion of the gas sensor element.

Herein, as the conventional art related to a gas sensor element with a porous protective layer, Patent Document 1 discloses a gas sensor element in which the periphery of the element is surrounded by a porous protective layer made of alumina to suppress collision of water droplets. In addition, Patent Document 2 discloses a gas sensor element with a porous protective layer that is made of a single material of silicon carbide or aluminum nitride or a mixed material thereof with other ceramic materials. Further, Patent Document 3 discloses a gas sensor element that has, on a gas introduction outer surface, through which a measurement target gas is introduced, of a diffusive resistance layer of the main body portion of the element, a porous protective layer for trapping poisonous components in the measurement target gas, and a surface protective layer that is formed on the porous protective layer, has water repellency at a high temperature at which a solid electrolyte body becomes active, and has smaller porosity than the porous protective layer.

As described above, a variety of improvements has been made to a porous protective layer that is provided around a detection portion to improve the water-resistant property of gas sensor elements. In particular, a technology related to a material that is applied to the porous protective layer has been mainly developed. It should be noted that in Patent Document 3, the surface roughness of the surface protective layer, which has smaller porosity than the porous protective layer, is defined to prevent cracking of the element, which would otherwise occur due to thermal shock when the element becomes wet, whereby the water repellency of the surface protective layer can be ensured.

By configuring a porous protective layer of a gas sensor element such that it repels condensed water in exhaust gas, it becomes possible to significantly reduce thermal shock that can be generated in the porous protective layer or the gas sensor element and also suppress infiltration of the condensed water, thereby solving the problem that the detection portion may become poisoned.

Regarding the water repellency of the porous protective layer, the inventors have found that a porous protective layer with excellent water repellency can be obtained through a different approach from that of the conventional art.

RELATED ART DOCUMENTS

Patent Documents

Patent Document 1: JP 2009-80110 A
Patent Document 2: JP 2011-237222 A
Patent Document 3: JP 2012-93330 A

SUMMARY

The present invention has been made in view of the foregoing problems, and it is an object of the present invention to provide a gas sensor element having a porous protective layer with more excellent water repellency.

In order to achieve the above object, a gas sensor element in accordance with the present invention includes a detection portion, which has a stack of a solid electrolyte body having at least a pair of electrodes on opposite sides thereof and a heat generating body including a heat generating source, and a porous protective layer formed around the detection portion. The porous protective layer has thermal conductivity $\lambda$ in the range of 0.2 to 5 W/mK, and has $\lambda Cp\rho$, which is the product of the thermal conductivity $\lambda$(W/mK), density $\rho$(g/m$^3$), and specific heat Cp(J/gK), in the range of $5.3 \times 10^5$ to $2.1 \times 10^7$ WJ/m$^4$K$^2$.

In the gas sensor element in accordance with the present invention, two physical values, which are the thermal conductivity and the $\lambda Cp\rho$ value ($\lambda$: thermal conductivity (W/mK), $\rho$: density (g/m$^3$), and Cp: specific heat (J/gK)) of the porous protective layer, are focused, and the numerical ranges of such values are defined to ensure more excellent water repellency of the porous protective layer.

The thermal conductivity of the porous protective layer determines the transfer speed of heat from the porous protective layer to condensed water, and the speed determines the easiness of forming a steam film. The fact that a steam film can be easily formed means that the porous protective layer has excellent water repellency. In addition to the easiness of forming a steam film, the amount of heat that is necessary to form a steam film is also an important factor. That is, the porous protective layer can exhibit excellent water repellency only when it has a physical value with which an amount of heat that is necessary to form a steam film can be generated.

The inventors have found that the water repellent performance of the porous protective layer can be identified with high accuracy when the physical value corresponding to the amount of heat is represented by the product of thermal conductivity, density, and specific heat.

The water repellency of the porous protective layer is obtained by a film boiling phenomenon (i.e., Leidenfrost phenomenon). The Leidenfrost phenomenon herein is a phenomenon that when a water droplet contacts the surface of the porous protective layer at a high temperature, the surface of the water droplet evaporates instantaneously, and the evaporated steam forms a shielding layer between the surface of the porous protective layer and the water droplet. Due to the Leidenfrost phenomenon, even when a water droplet sticks to the surface of the porous protective layer, the water droplet is instantaneously separated from the surface of the porous protective layer. This means that water repellency is exhibited.

The thermal conductivity $\lambda$ is defined in the range of 0.2 to 5 W/mK. Herein, when the thermal conductivity $\lambda$ is in the range of greater than or equal to 0.2 W/mK, a film boiling phenomenon occurs and water repellency is thus exhibited. Thus, the lower limit value of the thermal conductivity is defined as 0.2 W/mK. In addition to the water repellency, response characteristics are another important characteristics of the gas sensor element. From the perspective of the response characteristics, the upper limit value of the thermal conductivity is defined as 5 W/mK. It has been known that the thermal conductivity and the porosity of a porous protective layer have a correlation, and likewise, the response characteristics of a gas sensor element and the porosity of a porous protective layer also have a correlation.

The inventors have identified that when the thermal conductivity of the porous protective layer is in the aforementioned numerical range at a temperature in the range of 400 to 850° C. in which the gas sensor is controlled, excellent water repellency is obtained.

Meanwhile, the $\lambda Cp\rho$ value is defined in the range of $5.3 \times 10^5$ to $2.1 \times 10^7$ WJ/m$^4$K$^2$. Herein, at a temperature of less than or equal to 850° C. to which the gas sensor element is exposed, a film boiling phenomenon occurs and water repellency is thus exhibited if the $\lambda Cp\rho$ value is in the range of greater than or equal to $5.3 \times 10^5$ WJ/m$^4$K$^2$. Thus, the lower limit value of the $\lambda Cp\rho$ value is defined as $5.3 \times 10^5$ WJ/m$^4$K$^2$. Meanwhile, from the perspective of the response characteristics, the upper limit value of the $\lambda Cp\rho$ value is defined as $2.1 \times 10^7$ WJ/m$^4$K$^2$.

According to the gas sensor element of the present invention, defining the two physical values: thermal conductivity and the $\lambda Cp\rho$ value ($\lambda$: thermal conductivity (W/mK), $\rho$: density (g/m$^3$), and Cp: specific heat (J/gK)) of the porous protective layer in predetermined numerical ranges can provide a gas sensor element with excellent water repellency and response characteristics.

The inventors have identified that the thermal conductivity $\lambda$ in the range of 0.2 to 5 W/mK corresponds to the porosity in the range of 10 to 50% of the porous protective layer. Further, the inventors have also identified that the $\lambda Cp\rho$ value in the range of $5.3 \times 10^5$ to $2.1 \times 10^7$ WJ/m$^4$K$^2$ corresponds to the porosity in the range of 10 to 50% of the porous protective layer. It should be noted that the porosity of the porous protective layer is desirably adjusted to the range of about 30% or the range of 20 to 50% of the aforementioned numerical range, in particular.

As a preferred embodiment of the gas sensor element of the present invention, the porous protective layer may further have a capillary radius in the range of 0.01 to 10 µm.

As a result of verifying the relationship between the capillary radius and the gas response time of the porous protective layer, a result was obtained such that the gas response time becomes shorter as the capillary radius is larger, and the gas response time is saturated at the shortest time when the capillary radius is 0.01 µM. Based on such experimental results, the lower limit value of the capillary radius is defined as 0.01 µm.

Meanwhile, as a result of verifying the relationship between the capillary radius of the porous protective layer and the infiltration distance of water droplets, the inventors verified that the infiltration distance becomes longer as the capillary radius is larger, and the infiltration distance is greater than or equal to 700 µm, which is currently considered to be the maximum value of the thickness of the porous protective layer, when the capillary radius is 10 µm. Thus, the upper limit value of the capillary radius is defined as 10 µm based on the experimental results.

Herein, the aforementioned porous protective layer can have any of the following two structures.

The first structure is a single-layer structure formed of an aggregate containing alumina and a coating material containing silica. A number of aggregates containing alumina are linked by silica, which is a binder, whereby a porous protective layer with a single-layer structure is formed.

Meanwhile, the second structure is a stacked structure of a lower layer in contact with the detection portion located in the gas sensor element, and an upper layer in contact with the outside of the gas sensor element. The porosity of the upper layer is relatively lower than that of the lower layer. At least the upper layer has a two-layer structure formed of an aggregate containing alumina and a coating material containing silica.

When the upper layer to be in contact with condensed water is formed using an aggregate containing alumina and a coating material containing silica so that the upper layer becomes relatively denser than the lower layer, the upper layer can surely have water repellency, and the lower layer can surely have a property of trapping poisonous substances as the lower layer becomes more porous than and has a larger specific surface area than the upper layer.

As can be understood from the foregoing description, according to the gas sensor element of the present invention, defining the two physical values: thermal conductivity and the $\lambda Cp\rho$ value ($\lambda$: thermal conductivity (W/mK), $\rho$: density (g/m$^3$), Cp: specific heat (J/gK)) of the porous protective layer in predetermined numerical ranges can provide a gas sensor element with excellent water repellency and response characteristics.

Thus, the operation and advantageous effects of an exemplary embodiment are that defining the product of the thermal conductivity, density, and specific heat can form a shielding film between the surface of the porous protective film and a water droplet and thus can provide more excellent water repellency of the porous protective film. The operation and advantageous effects of another exemplary embodiment are that defining the capillary radius of the porous protective film allows the gas response time to be saturated and can maximize the infiltration distance of water droplets. The operation and advantageous effects of another exemplary embodiment are that defining the porosity of the porous protective film can optimize the response characteristics and thermal conductivity of the gas sensor element. The operation and advantageous effects of another exemplary embodiment are that covering an aggregate with high fire resistance and high hardness with a coating material using a sol-gel method can form a porous protective film with a large specific surface area. The operation and advantageous effects of another exemplary embodiment are that the upper layer to be in contact with condensed water is formed using an aggregate containing alumina and a coating material containing silica sol so that the upper layer becomes relatively denser than the lower layer, whereby the upper layer can surely have water repellency, and the lower layer can surely have a property of trapping poisonous substances as the lower layer becomes more porous than and has a larger specific surface area than the upper layer.

DETAILED DESCRIPTION OF THE EMBODIMENT(S)

Hereinafter, embodiments of a gas sensor element of the present invention will be described with reference to the drawings.

Embodiment 1 of Gas Sensor Element

Figure 1:
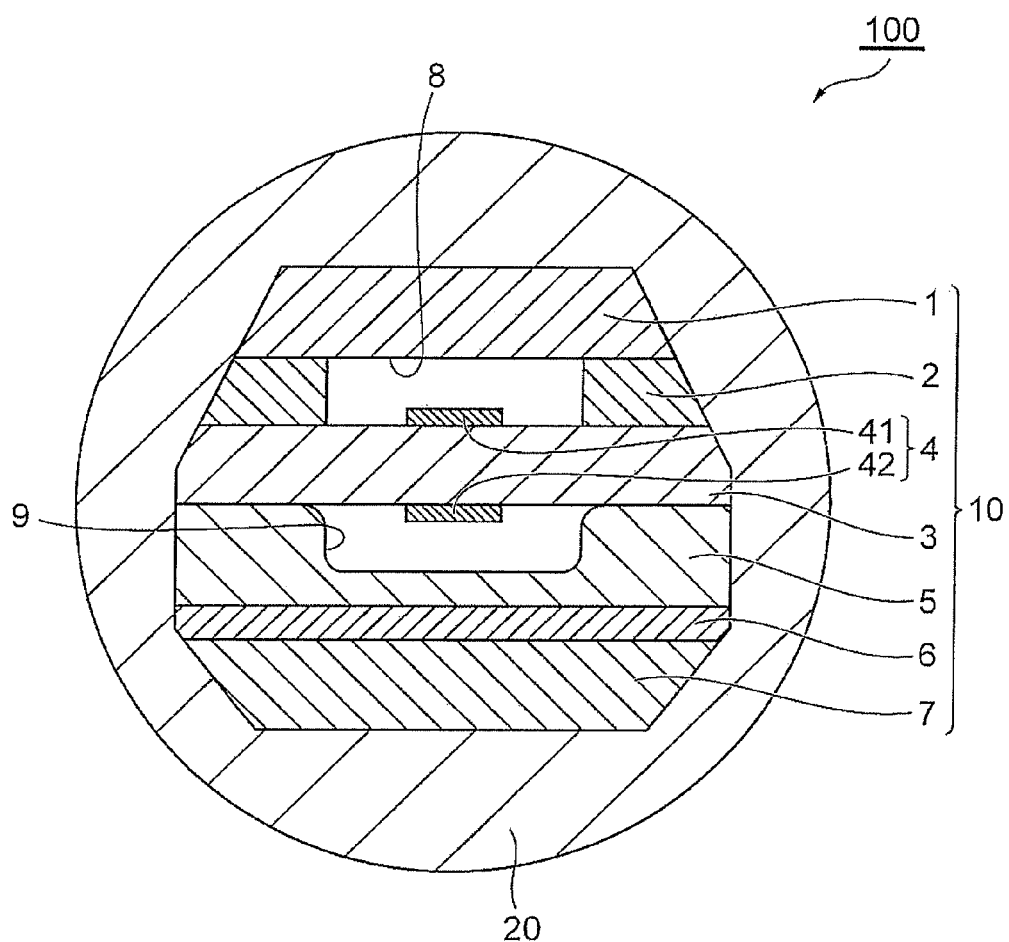
FIG. 1 is a schematic diagram illustrating Embodiment 1 of a gas sensor element of the present invention.

FIG. 1 is a schematic diagram illustrating Embodiment 1 of a gas sensor element of the present invention. A gas sensor element 100 shown in FIG. 1 generally includes a detection portion 10 that detects the concentration of oxygen in exhaust gas, and a porous protective layer 20 that protects the periphery of the detection portion 10 against moisture in the exhaust gas and thus suppresses generation of abnormal outputs that would otherwise occur due to a temperature drop of the detection portion 10 resulting from the moisture reaching the detection portion 10, and also traps hydrogen gas, carbon monoxide gas, and the like that pass therethrough.

The detection portion 10 generally includes a solid electrolyte layer 3, which has on opposite sides thereof a pair of electrodes 4 including an electrode 41 on the measurement target gas side and an electrode 42 on the reference gas side, a porous diffusive resistance layer 2 that surrounds the electrode 41 on the measurement target gas side via a measurement target gas space 8, a shielding layer 1 that defines the measurement target gas space 8 together with the porous diffusive resistance layer 2, a reference gas space protective layer 5 that surrounds the electrode 42 on the reference gas side via a reference gas space 9, and a heat generating source 6 and a heat generating source substrate 7.

The heat generating source 6 includes a heater that is a heat generating body, and forms a heating region of the gas sensor element 100 so that it is heat-controlled to attain the activation temperature thereof.

The detection portion 10 has, in the cross-sectional shape shown in the drawing, corner portions that are cut out in taper shapes. With such cutout portions, the thickness of the porous protective layer 20 at the corresponding portions of the detection portion 10 is ensured.

The solid electrolyte layer 3 is formed of zirconia, and the electrode 41 on measurement target gas side and the electrode 42 on the reference gas side are each formed of platinum. In addition, the shielding layer 1 and the reference gas space protective layer 5 each exhibit a gas impermeable internal structure, and are formed of alumina.

Voltage at which the oxygen concentration difference and current have a linear correlation is applied across the pair of electrodes 4, and a measurement target gas is made to contact the electrode 41 on the measurement target gas side, while a reference gas, such as air, is made to contact the electrode 42 on the reference gas side. Then, the value of current generated between the electrodes in accordance with each oxygen concentration difference is measured, so that the air-fuel ratio of the vehicle engine can be identified on the basis of the measured current.

The porous diffusive resistance layer 2 is provided at a position that defines the measurement target gas space 8 around the electrode 41 on the measurement target gas side to suppress the amount of the measurement target gas introduced to the electrode 41 on the measurement target gas side, and is configured to further introduce hydrogen gas, carbon monoxide gas, oxygen gas, and the like of the exhaust gas, which have been introduced via the porous protective layer 20 around the detection portion 10, into the measurement target gas space 8 via the porous diffusive resistance layer 2.

The porous protective layer 20 is a porous layer containing alumina, which has noble metal catalyst particles (not shown) supported on its surface, and silica sol. The noble metal catalyst particles in the porous protective layer 20 may be distributed across the entire region of the porous protective layer 20 or distributed only in the lateral region thereof corresponding to the porous diffusive resistance layer 2 in proximity to the electrode 41 on the measurement target gas side. Alternatively, the amount of noble metal catalyst particles that are supported in the porous protective layer 20 may be distributed such that a relatively larger amount of noble metal catalyst particles are supported in a region corresponding to the porous diffusive resistance layer 2, for example. Herein, as the noble metal catalyst particles, palladium or rhodium may be used alone, or an alloy containing two or more of palladium, rhodium, and platinum may be used.

The porous protective layer 20 can be produced using a so-called dip method that includes repeated operations of dipping the detection portion 10 in a slurry containing an aggregate, which contains at least one of alumina, spinel, silicon carbide, or aluminum nitride, and a coating material, which contains at least one of silica, alumina, titania, zirconia, antimony oxide, or zinc oxide, and taking the detection portion 10 out of the slurry and drying it until a predetermined thickness is obtained. Alternatively, the porous protective layer 20 can be produced using a flame spraying method that is suitable for producing a dense layer. Regarding alumina, if particles that contain at least one of, besides α-alumina, γ-alumina, θ-alumina, or spinel are applied, it is possible to form the porous protective layer 20 with a large specific surface area, thereby improving the property of trapping poisonous substances. In particular, a slurry that contains an aggregate containing alumina and a coating material containing silica is preferably used to produce the porous protective layer 20.

The porous protective layer 20 has thermal conductivity $\lambda$ set in the range of 0.2 to 5 W/mK, and further has $\lambda Cp\rho$, which is the product of the thermal conductivity $\lambda$(W/mK), density $\rho$(g/m$^3$), and specific heat Cp(J/gK), set in the range of $5.3 \times 10^5$ to $2.1 \times 10^7$ WJ/m$^4$K$^2$.

When the thermal conductivity $\lambda$ and the $\lambda Cp\rho$ value are set in the aforementioned numerical ranges, it is possible to provide excellent water repellency and response characteristics due to the Leidenfrost phenomenon in the temperature range of 400 to 850° C. at which the gas sensor element 100 is controlled, in particular.

The capillary radius of the porous protective layer 20 is preferably set in the range of 0.01 to 10 μm.

When the capillary radius of the porous protective layer 20 is set in the aforementioned numerical range, the gas response time is saturated at about 300 msec, which is the shortest time, with a capillary radius of 0.01 μm, in particular. Further, regarding the infiltration distance of the condensed water, the infiltration distance is 700 μm, which is currently considered to be the maximum value of the thickness of the porous protective layer, with a capillary radius of 10 μm, in particular. Thus, when the capillary radius of the porous protective layer 20 is set in the range of 0.01 to 10 μm, the response characteristics and the infiltration distance of water droplets can be controlled within optimal ranges.

Embodiment 2 of Gas Sensor Element

Figure 2:
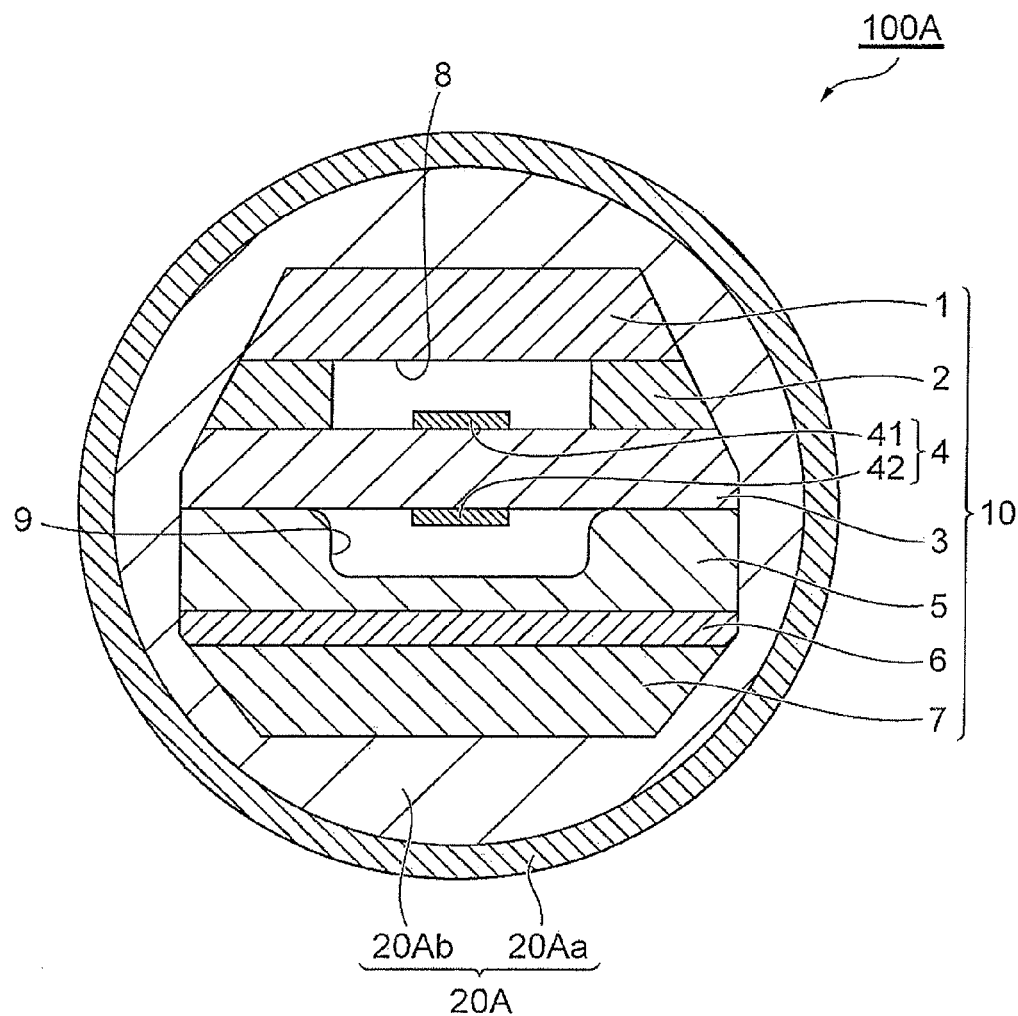
FIG. 2 is a schematic diagram illustrating Embodiment 2 of a gas sensor element of the present invention.

FIG. 2 is a schematic diagram illustrating Embodiment 2 of a gas sensor element in accordance with the present invention. A gas sensor element 100A shown in FIG. 2 includes a porous protective layer 20A with a two-layer stacked structure of a lower layer 20Ab in contact with the detection portion 10 and an upper layer 20Aa in contact with the outside.

In the porous protective layer 20A, the porosity of the upper layer 20Aa is relatively lower than that of the lower layer 20Ab, and at least the upper layer 20Aa is formed using an aggregate, which contains at least one of alumina, spinel, silicon carbide, or aluminum nitride, and a coating material, which contains at least one of silica, alumina, titania, zirconia, antimony oxide, or zinc oxide. When the upper layer 20Aa, which is in direct contact with condensed water, is formed using an aggregate containing alumina and silica sol, and is formed as a relatively denser layer than the lower layer 20Ab, the upper layer 20Aa can surely have water repellency, and the lower layer 20Ab can surely have a property of trapping poisonous substances as the lower layer 20Ab becomes more porous than and has a larger specific surface area than the upper layer 20Aa. In particular, a slurry that contains an aggregate containing alumina and a coating material containing silica is preferably used to produce the porous protective layer 20Aa.

If the porous protective layer 20A has the thermal conductivity $\lambda$ set in the range of 0.2 to 5 W/mK, and has $\lambda Cp\rho$, which is the product of the thermal conductivity $\lambda$(W/mK), density $\rho$(g/m$^3$), and specific heat Cp(J/gK), set in the range of $5.3 \times 10^5$ to $2.1 \times 10^7$ WJ/m$^4$K$^2$, it is also possible to provide the gas sensor element 100A with excellent water repellency and response characteristics.

[Experiments of Identifying the Relationship Between the Ambient Temperature of a Gas Sensor that Satisfies a Water Repelling Amount of 3 μL and the Thermal Conductivity of a Porous Protective Layer, Experiments of Identifying the Relationship Between the Ambient Temperature of a Gas Sensor that Satisfies a Water Repelling Amount of 3 μL and the $\lambda Cp\rho$ Value of a Porous Protective Layer, and Results Thereof]

The inventors conducted experiments of identifying the relationship between the ambient temperature and the thermal conductivity and the $\lambda Cp\rho$ value of a porous protective layer that are two physical values serving as indices of excellent water repellency against a water droplet with an amount of 3 μL, which is required of the porous protective layer, in the temperature range of 400 to 850° C. at which a gas sensor is controlled.

Herein, the porous protective layer has a single-layer structure shown in FIG. 1. A slurry was generated by dispersing 8 μm α-alumina, 20 mass % silica sol, and a dispersant (PVA) in water, and, for a region in which the porosity is greater than 30%, the slurry was made to stick to the periphery of the detection portion of the gas sensor element using a dip method, and then, baking was performed in the atmosphere at 900° C. for two hours to produce a porous protective layer, while for a region in which the porosity is the range of less than or equal to 30%, a porous protective layer with similar specifications was produced using a flame spraying method.

Figure 3:
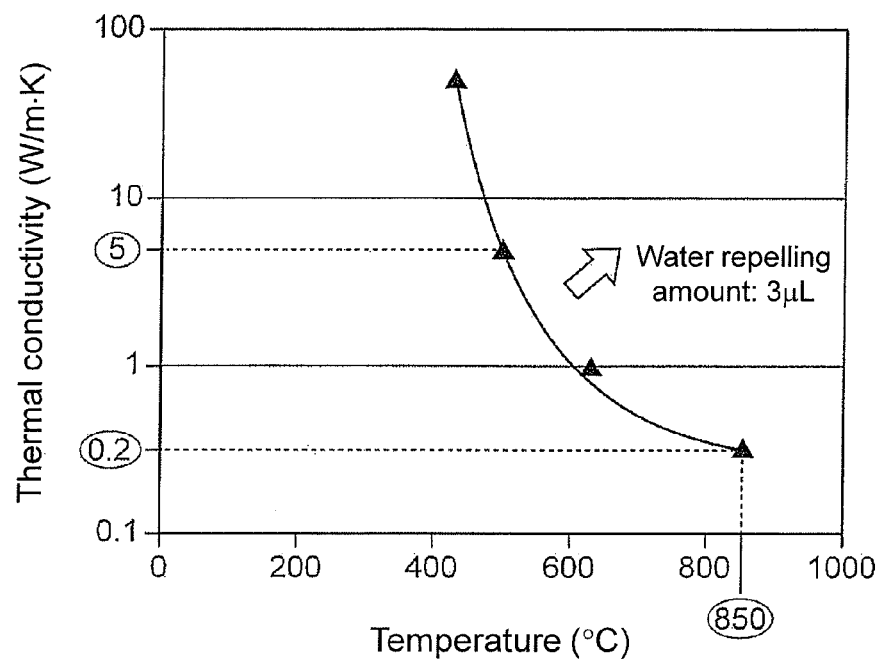
FIG. 3 is a diagram showing experimental results that identify the relationship between the ambient temperature of a gas sensor that satisfies a water repelling amount of 3 µL and the thermal conductivity of a porous protective layer.
Figure 4:
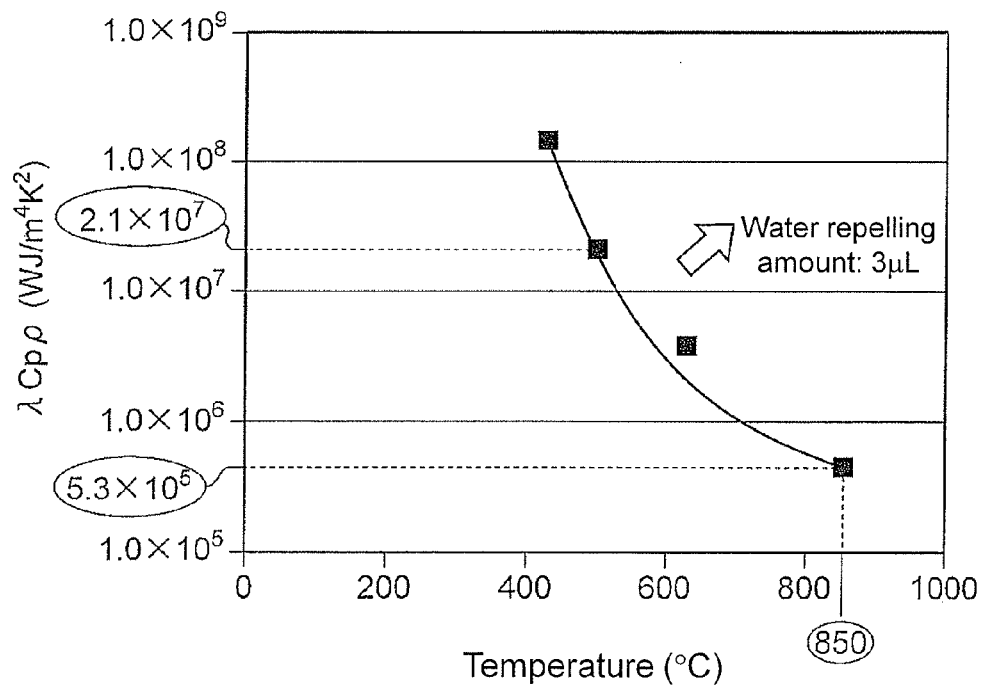
FIG. 4 is a diagram showing experimental results that identify the relationship between the ambient temperature of a gas sensor that satisfies a water repelling amount of 3 µL and the λCpρ value of a porous protective layer.

FIG. 3 is a diagram showing experimental results that identify the relationship between the ambient temperature of a gas sensor that satisfies a water repelling amount of 3 μL and the thermal conductivity of a porous protective layer. FIG. 4 is a diagram showing experimental results that identify the relationship between the ambient temperature of a gas sensor that satisfies a water repelling amount of 3 μL and the $\lambda Cp\rho$ value of a porous protective layer.

FIG. 3 can confirm that the thermal conductivity decreases in a quadratic curve manner with respect to the ambient temperature, and the thermal conductivity is 0.2 W/mK at a temperature of 850° C., while the thermal conductivity is 5 W/mK at a temperature of about 500° C. (i.e., a temperature of greater than or equal to 400° C.).

Meanwhile, FIG. 4 can confirm that the $\lambda Cp\rho$ value also decreases in a quadratic curve manner with respect to the ambient temperature, and the $\lambda Cp\rho$ value is $5.3 \times 10^5$ WJ/m$^4$K$^2$ at a temperature of 850° C., while the $\lambda Cp\rho$ value is $2.1 \times 10^7$ WJ/m$^4$K$^2$ at a temperature of about 500° C. (i.e., a temperature of greater than or equal to 400° C.).

[Experiments of Identifying the Relationship Among the Porosity, Thermal Conductivity, and Response Characteristics, Experiments of Identifying the Relationship Among the Porosity, $\lambda Cp\rho$ Value, and Response Characteristics, and Results Thereof]

The inventors conducted experiments of identifying the relationship among each porosity, thermal conductivity, and response characteristics, and the relationship among each porosity, $\lambda Cp\rho$ value, and response characteristics by changing the porosity. It should be noted that the method for producing a porous protective layer and the usage thereof are the same as those in the aforementioned experiments.

Figure 5:
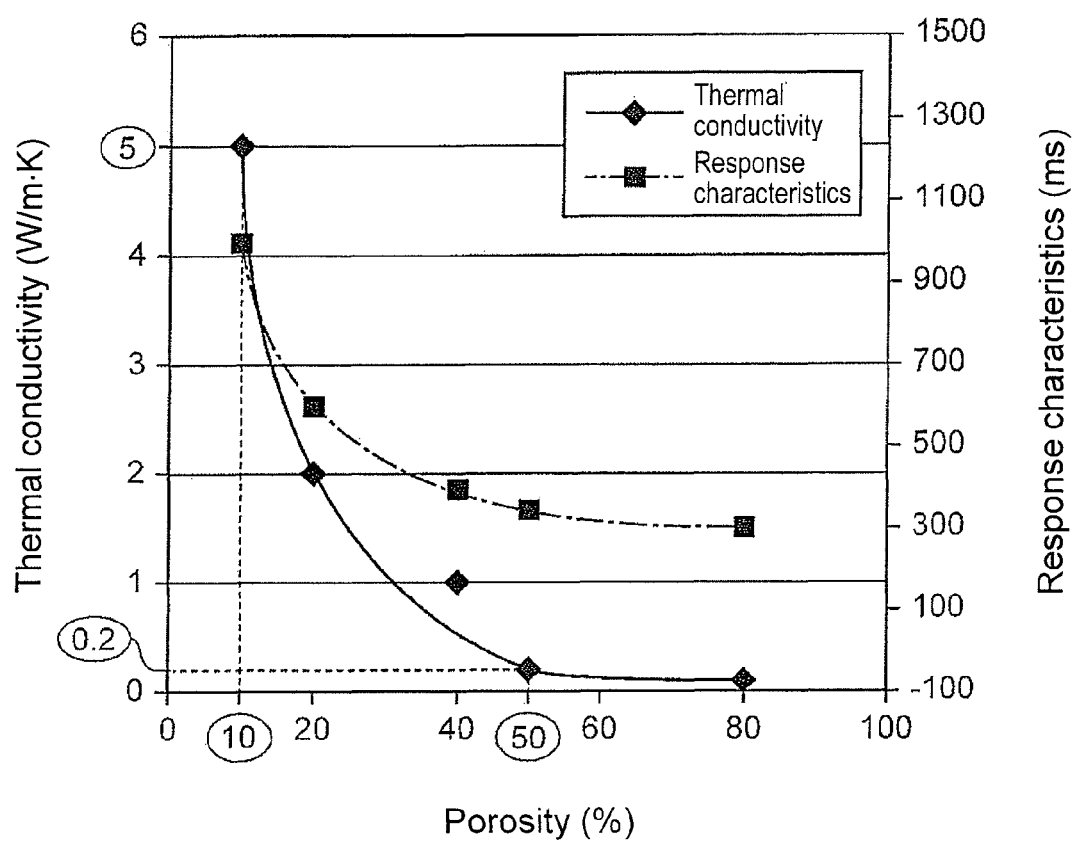
FIG. 5 is a diagram showing experimental results that identify the relationship among the porosity, thermal conductivity, and response characteristics.
Figure 6:
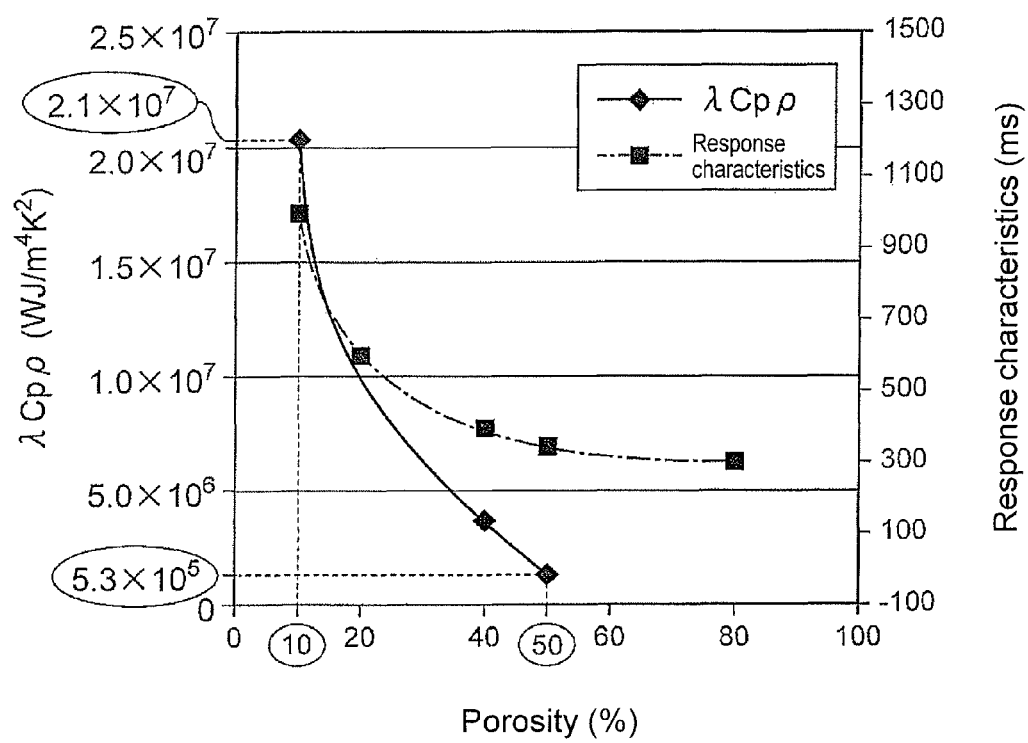
FIG. 6 is a diagram showing experimental results that identify the relationship among the porosity, λCpρ value, and response characteristics.

FIG. 5 is a diagram showing experimental results that identify the relationship among the porosity, thermal conductivity, and response characteristics. FIG. 6 is a diagram showing experimental results that identify the relationship among the porosity, λCpρ value, and response characteristics.

FIG. 5 can confirm that the thermal conductivity is 0.2 W/mK when the porosity is 50%, while the thermal conductivity is 5 W/mK when the porosity is 10%.

From FIG. 5, it is recognized that as the response characteristics become too large when the porosity is in the range of less than 10% (i.e., when the thermal conductivity is in the range of greater than 5 W/mK), the thermal conductivity is desirably not greater than 5 W/mK.

The experimental results shown in FIGS. 3 and 5 can confirm that a preferable range of the thermal conductivity of the porous protective layer can be defined in the range of 0.2 to 5 W/mK from the perspective of water repellency and response characteristics.

Meanwhile, FIG. 6 can confirm that the λCpρ value is $5.3 \times 10^5$ WJ/m$^4$K$^2$ when the porosity is 50%, while the λCpρ value is $2.1 \times 10^7$ WJ/m$^4$K$^2$ when the porosity is 10%.

From FIG. 6, it is recognized that as the response characteristics become too large when the porosity is in the range of less than 10% (i.e., the λCpρ value is in the range of greater than $2.1 \times 10^7$ WJ/m$^4$K$^2$), the λCpρ value is desirably not greater than $2.1 \times 10^7$ WJ/m$^4$K$^2$.

The experimental results shown in FIGS. 4 and 6 can confirm that a preferable range of the λCpρ value of the porous protective layer can be defined in the range of $5.3 \times 10^5$ to $2.1 \times 10^7$ WJ/m$^4$K$^2$ from the perspective of water repellency and response characteristics.

[Experiments Related to the Relationship Between the Ratio of a Water Droplet Cross-Section and Water Repellency, and Results Thereof]

The inventors conducted experiments of identifying the relationship between the ratio of a water droplet cross-section and water repellency. The experiments verify the ratio between the contact area of a solid liquid on the porous protective layer, which exhibits water repellency upon occurrence of a film boiling phenomenon when a water droplet with an amount of 3 μL is dropped, which is required of the porous protective layer, and a water droplet cross-section. Table 1 below shows the results of the verification.

TABLE 1

| Ratio of Water Droplet Cross-Section | Water Repellency |
|---|---|
| 0.01 | o |
| 0.2 | o |
| 1 | o |
| 2 | o |
| 4 | o |
| 5 | x |
| 7 | x |

Notes:
"o" indicates that a water-repellent phenomenon occurs on the entire surface of the porous protective layer, while "x" indicates that a water-repellent phenomenon does not occur on parts of the surface of the porous protective layer.

From Table 1, it is found that when the ratio of a water droplet cross-section becomes five times as large or more, the temperature of the surface of the porous protective layer drops as a steam film is formed due to an increased contact area of the solid liquid, so that a steam film becomes difficult to be formed on parts of the layer, and thus, such parts do not exhibit a water-repellent phenomenon.

[Experiments Related to a Temperature Change of the Surface of a Porous Protective Layer and Water Repellency and Results Thereof]

The inventors conducted experiments of identifying the relationship between a temperature change of the surface of a porous protective layer and water repellency. The experiments verify the degree of a temperature change of the surface of a porous protective layer that exhibits water repellency upon occurrence of a film boiling phenomenon when a water droplet with a drop amount of 3 μL is dropped, which is required of the porous protective layer. Table 2 below shows the results of verification.

TABLE 2

| Temperature Change of Surface of Porous Protective Layer | Water Repellency |
|---|---|
| 100 | o |
| 130 | o |
| 150 | o |
| 200 | x |

Notes:
"o" indicates that a water-repellent phenomenon occurs on the entire surface of the porous protective layer, while "x" indicates that a water-repellent phenomenon does not occur on parts of the surface of the porous protectivelayer.

From Table 2, it is found that when the temperature change of the surface of the porous protective layer exceeds 150° C. (when the amount of the temperature change is 150° C. or more), it becomes difficult to form a steam film or maintain the steam film. Thus, water repellency is not exhibited.

[Experiments of Identifying the Relationship Among the Capillary Radius, Gas Response Time, and Infiltration Distance, and Results Thereof]

The inventors further conducted experiments of identifying the relationship among the capillary radius, gas response time, and infiltration distance. Herein, the capillary radius was defined based on the result of a measurement conducted by scrapping a part of a porous protective layer and measuring the distribution of pores using a mercury porosimeter.

As a method for evaluating the gas response characteristics, a sensor output obtained by switching gas between A/F13 (rich side) and A/F18 (lean side) for a specimen of a gas sensor element with a porous protective layer was used, and 63% response time of the obtained sensor output was evaluated. Herein, $N_2$, $C_3H_8$, and $O_2$ were used as the base gas, and $O_2$ was used as the injection gas.

Figure 7:
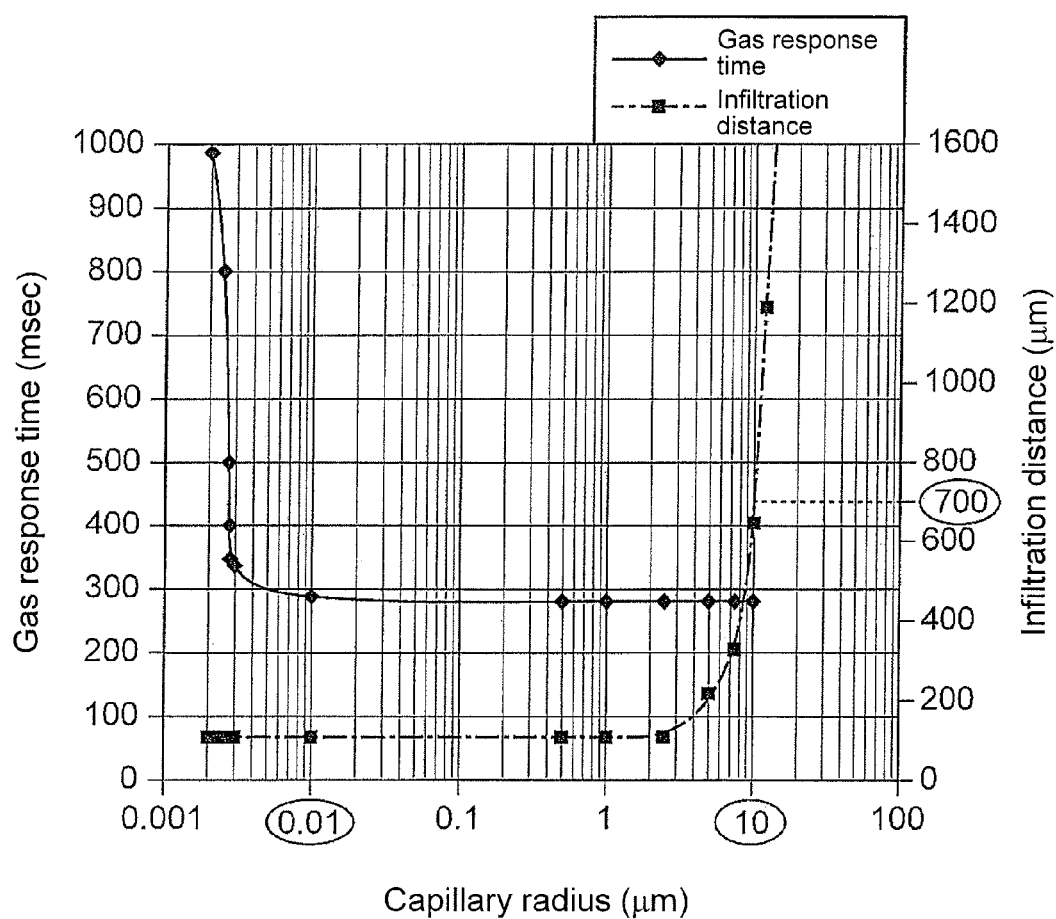
FIG. 7 is a diagram showing experimental results that identify the relationship among the capillary radius, gas response time, and infiltration distance.

Meanwhile, as a method for evaluating the infiltration distance, a 0.3 μL iron chloride aqueous solution that simulates water was discharged to a specimen using a dispenser, and the specimen was potted in resin. Then, the cross-section of the porous protective layer was observed to measure the infiltration distance. FIG. 7 shows the results of the measurement.

FIG. 7 can confirm that the gas response time decreases in a curved manner with an increased capillary radius, and the gas response time is saturated at about 300 msec, which is the shortest time, when the capillary radius is 0.01 μm. The infiltration distance of condensed water increases in a curved manner with an increased capillary radius, and the infiltration distance is 700 μm, which is currently considered to be the maximum value of the thickness of the porous protective layer, when the capillary radius is 10 μm. From such results, it is found that the response characteristics and the infiltration distance of water droplets can be controlled within optimal ranges when the capillary radius of the porous protective layer is set in the range of 0.01 to 10 μm.

Although the embodiments of the present invention have been described in detail with reference to the drawings, specific configurations are not limited thereto. The present invention includes any design change and the like that may occur within the spirit and scope of the present invention.

DESCRIPTION OF SYMBOLS

1 Shielding layer
2 Porous diffusive resistance layer
3 Solid electrolyte layer
4 Pair of electrodes
41 Electrode on the measurement target gas side
42 Electrode on the reference gas side
5 Reference gas space protective layer
6 Heat generating source (heater)
7 Heat generating source substrate
8 Measurement target gas space
9 Reference gas space
10 Detection portion
20,20A Porous protective layer
20Aa Upper layer
20Ab Lower layer
100,100A Gas sensor element

What is claimed is:

1. A gas sensor element comprising:
a detection portion having a stack of a solid electrolyte body and a heat generating body, the solid electrolyte body having at least a pair of electrodes on opposite sides thereof and the heat generating body including a heat generating source; and
a porous protective layer formed around the detection portion and including an aggregate and a coating material, wherein
the porous protective layer, as a whole, has a thermal conductivity $\lambda$ in a range of 0.2 to 5 W/mK, and has $\lambda Cp\rho$ in a range of $5.3 \times 10^5$ to $2.1 \times 10^7$ WJ/m$^4$K$^2$, the $\lambda Cp\rho$ being a product of the thermal conductivity $\lambda$(W/mK), density $\rho$(g/m$^3$), and specific heat Cp(J/gK).

2. The gas sensor element according to claim 1, wherein the porous protective layer, as a whole, has a porosity in a range of greater than or equal to 10 and less than 50%.

3. The gas sensor element according to claim 1, wherein the porous protective layer has a stacked structure of a lower layer and an upper layer, the lower layer being in contact with the detection portion located in the gas sensor element, and the upper layer facing an outside of the gas sensor element,
a porosity of the upper layer is relatively lower than a porosity of the lower layer, and
at least the upper layer has a two-layer structure including an aggregate and a coating material, the aggregate containing at least one of alumina, silicon carbide, spinel, or aluminum nitride, and the coating material containing at least one of silica, alumina, titania, zirconia, antimony oxide, or zinc oxide.

4. A gas sensor element comprising:
a detection portion having a stack of a solid electrolyte body and a heat generating body, the solid electrolyte body having at least a pair of electrodes on opposite sides thereof and the heat generating body including a heat generating source; and
a porous protective layer formed around the detection portion, wherein
the porous protective layer has a thermal conductivity $\lambda$ in a range of 0.2 to 5 W/mK, and has $\lambda Cp\rho$ in a range of $5.3 \times 10^5$ to $2.1 \times 10^7$ WJ/m$^4$K$^2$, the $\lambda Cp\rho$ being a product of the thermal conductivity $\lambda$(W/mK), density $\rho$(g/m$^3$), and specific heat Cp(J/gK), and
the porous protective layer further has a capillary radius in a range of 0.01 to 10 μm.

5. A gas sensor element comprising:
a detection portion having of a solid electrolyte body and a heat generating body, the solid electrolyte body having at least a pair of electrodes on opposite sides thereof and the heat generating body including a heat generating source; and
a porous protective layer formed around the detection portion, wherein
the porous protective layer has a thermal conductivity $\lambda$ in a range of 0.2 to 5 W/mK, and has $\lambda Cp\rho$ in a range of $5.3 \times 10^5$ to $2.1 \times 10^7$ WJ/m$^4$K$^2$, the $\lambda Cp\rho$ being a product of the thermal conduct $\lambda$(W/mK), density $\rho$(g/m$^3$), and specific heat Cp(J/gK), and
the porous protective layer has a single-layer structure including an aggregate and a coating material, the aggregate containing at least one of silicon carbide or aluminum nitride, and the coating material containing at least one of silica or antimony oxide.

* * * * *